United States Patent
Sato et al.

(10) Patent No.: US 7,402,610 B2
(45) Date of Patent: Jul. 22, 2008

(54) CARBONYL COMPOUND CONTAINING LONG-CHAIN BRANCHED ALKYL GROUP

(75) Inventors: Haruhito Sato, Ichihara (JP); Takashi Kashiwamura, Ichihara (JP); Takuji Okamoto, Ichihara (JP); Kiyohiko Yokota, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/587,395

(22) PCT Filed: Jan. 28, 2005

(86) PCT No.: PCT/JP2005/001223

§ 371 (c)(1),
(2), (4) Date: Jul. 2, 2007

(87) PCT Pub. No.: WO2005/077876

PCT Pub. Date: Aug. 25, 2005

(65) Prior Publication Data

US 2007/0282123 A1    Dec. 6, 2007

(30) Foreign Application Priority Data

Jan. 28, 2004    (JP)    ............... 2004-020493

(51) Int. Cl.
*A61K 31/20* (2006.01)
*C07C 59/00* (2006.01)
(52) U.S. Cl. ..................... 514/558; 554/213
(58) Field of Classification Search ............ None
See application file for complete search history.

(56) References Cited

U.S. PATENT DOCUMENTS

| | | | |
|---|---|---|---|
| 5,191,072 A * | 3/1993 | Hasegawa et al. | ........... 536/117 |
| 5,488,121 A | 1/1996 | O'Lenick | |
| 5,587,155 A * | 12/1996 | Ochiai et al. | ........... 424/70.28 |
| 5,639,791 A | 6/1997 | O'Lenick | |

FOREIGN PATENT DOCUMENTS

| | | |
|---|---|---|
| EP | 0 444 208 A1 | 9/1991 |
| GB | 1 239 394 | 7/1971 |
| JP | 63-203645 | 8/1988 |
| JP | 05-098276 | 4/1993 |
| JP | 05-230490 | 9/1993 |
| JP | 08-127963 | 5/1996 |
| JP | 08-183724 | 7/1996 |
| JP | 11-061646 | 3/1999 |
| JP | 2000-514470 | 10/2000 |
| JP | 57-200325 | 12/2002 |
| WO | WO 94/02111 | 2/1994 |

OTHER PUBLICATIONS

Polgar et al, Journal of the Chemical Society, Long-chain Acids Containing a Quaternary C Atom. Part II, 1943, pp. 615-619.*
Karinen, Reetta S. et al., "Catalytic synthesis of a novel tertiary ether, 3-methoxy-3-methyl heptane, from 1-butene", Journal of Molecular Catalysis A: Chemical, vol. 152, No. 1-2, pp. 253-255, 2000.
Sakurai, Toshio, "Shinpan Junkatsu no Butsuri Kagaku", Saiwai Shobo, pp. 200-205, 1978.
Edited by CSJ: The Chemical Society of Japan, "Jikken Kagaku Koza 21 Yuki Kagaku III", Dai 4 Han, Maruzen Co., Ltd., pp. 58-61, 19991.
N. Polgar, et al. "Long-chain acids containing a quaternary C atom. II", Journal of the Chemical Society, 1943, XP-002461228, 1 Page.

* cited by examiner

*Primary Examiner*—Paul A Zucker
(74) *Attorney, Agent, or Firm*—Oblon, Spivak, McClelland, Maier & Neustadt, P.C.

(57) ABSTRACT

A carbonyl compound represented by the following formula [1],

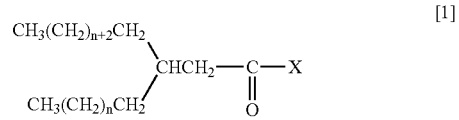

wherein X is hydrogen, a hydroxy group, an alkoxy group or a group derived from a polyol, and n, which is the same in each instance, is 4 to 30. Compositions comprising the compound, and method for making the compound.

16 Claims, 1 Drawing Sheet

CARBONYL COMPOUND CONTAINING LONG-CHAIN BRANCHED ALKYL GROUP

TECHNICAL FIELD

The invention pertains to a long-chain branched alkyl group-containing primary carbonyl compound. In particular, the invention pertains to a long-chain branched alkyl group-containing primary aldehyde, carboxylic acid, and carboxylate excelling in low temperature fluidity, possessing a high boiling point, and excelling in biodegradability, and to a synthetic lubricant comprising the same.

BACKGROUND ART

In order to disperse sludge and the like in engine oil to maintain cleanliness inside an engine, various lubricating oil additives represented by alkaline earth metal salts have been used. When these additives possess a high basicity, they are very economical due to a lower amount of required additive. However, the stability of these additives declines, resulting in problems such as gelling which forms a film on the surface of the engine and the like. For this reason, fatty acids are added to overcome these problems (for example, refer to Patent Document 1).

In regard to 2-cycle engine oils, since a portion of the engine oil is discharged along with the exhaust gas, engine oil used in outboard motors and so on has been required to possess biodegradability and heat stability.

As a carboxylic acid used as an additive in engine oil, tertiary carboxylic acids such as 3-methyloctane-3-carboxylic acid, secondary carboxylic acids such as 2-ethylhexanoic acid and isostearic acid, and the like can be used, and long-chain branched primary carboxylic acids having 20 or more carbon atoms are not known. These compounds do not fully exhibit the properties of low temperature fluidity, low volatility, biodegradability, and the like required for lubricating oil additives.

Various carboxylates are known to be used in the base stock of lubricating oils. For example, mineral oils are used in lubricating oils for chainsaws used in lumber logging. However, in recent years, in consideration of environmental problems, the use of biodegradable plant oils such as rapeseed oil (triglyceride of fatty acid) has been proposed (for example, refer to Patent Document 2).

Although these plant oils are biodegradable, they are unstable and possess poor low temperature properties due to unsaturated bonds contained therein, which limits their use as lubricating oils.

In order to improve thermal stability, the use of synthetic ester has been disclosed (for example, refer to Patent Document 3). However, good low temperature properties cannot be obtained.

An ester-type lubricating oil with improved flow characteristics at room temperature while ensuring biodegradability has been disclosed (for example, refer to Patent Document 4). However, since the carboxylic acid used possesses a comparatively short chain of up to 10 carbon atoms, the lubricating oil does not possess a satisfactory viscosity index, which is an important indicator of lubricating oil characteristics.

Although carboxylic acids used in paint coatings, epoxy resin reformers, plasticizers, cosmetic base materials, raw materials for stabilizers, and the like have been desired to be in a liquid state and possess a high boiling point in view of handling easiness, a compound satisfying these characteristics has not been known.

[Patent Document 1] JP-A-1988-203645
[Patent Document 2] JP-A-1993-230490
[Patent Document 3] JP-A-1993-98276
[Patent Document 4] JP-A-2000-514470

DISCLOSURE OF THE INVENTION

In view of the above, an objective of the invention is to provide a long-chain branched alkyl group-containing primary carbonyl compound (aldehyde, carboxylic acid, and carboxylate) excelling in low temperature fluidity and biodegradability and possessing a high boiling point.

As a result of extensive research in order to achieve the above objective, the inventors discovered that a branched alkyl chain containing aldehyde, carboxylic acid, and carboxylate having a long-chain linear alkyl group with a formyl group, carboxyl group, and ester group branched at the β-position, the main chain and branched chains having a specific relationship, excels in low temperature fluidity and biodegradability and has a high boiling point, thereby completing the invention.

In addition, the invention provides methods for producing the following long-chain branched alkyl group-containing primary carbonyl compound, synthetic lubricant, cosmetic base material, plasticizer, and carbonyl compound.

1. A carbonyl compound represented by the following formula [1],

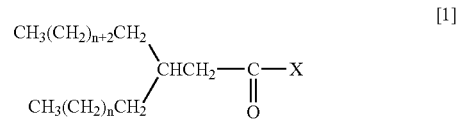

wherein X is hydrogen, a hydroxy group, an alkoxy group, or a group derived from a polyol, and n is 4 to 30.

2. The carbonyl compound according to 1 wherein n of the formula [1] is 4 to 20.
3. The carbonyl compound according to 1 wherein n of the formula [1] is an even number of 4 to 10.
4. The carbonyl compound according to 1 wherein n of the formula [1] is 6.
5. The carbonyl compound according to any one of 1 to 4 wherein X of the formula [1] is an alkoxy group (—OR) and R is a hydrocarbon group with 6 to 30 carbon atoms.
6. The carbonyl compound according to any one of 1 to 4 which is an ester compound derived from a hindered alcohol.
7. The carbonyl compound according to 6 wherein the hindered alcohol is a compound selected from trimethylolpropane, trimethylolethane, and neopentylglycol.
8. A synthetic lubricant comprising the carbonyl compound according to any one of 1 to 7.
9. A cosmetic base material comprising the carbonyl compound according to any one of 1 to 7.
10. A plasticizer comprising the carbonyl compound according to any one of 1 to 7.
11. A method for producing the carbonyl compound according to 1 comprising the steps of:
    (a) dimerizing a compound represented by CH$_3$(CH$_2$)$_{n+2}$CH$_2$CH=CH$_2$ (wherein n is 4 to 30) by using a metallocene catalyst to synthesize a vinylidene compound of the following formula [2], and (b) reacting the vinylidene compound of the following formula [2] with carbon monoxide and hydrogen under oxo reaction conditions to synthesize an aldehyde compound of the following formula [3].

12. The method according to 11 further comprising the step of:
(c) oxidizing the aldehyde compound of the formula [3] under oxidizing reaction conditions to synthesize a carboxylic compound of the following formula [4].

The invention provides a long-chain branched alkyl group-containing primary carbonyl compound excelling in low temperature fluidity and biodegradability and possessing a high boiling point.

BEST MODE FOR CARRYING OUT THE INVENTION

Figure 1:
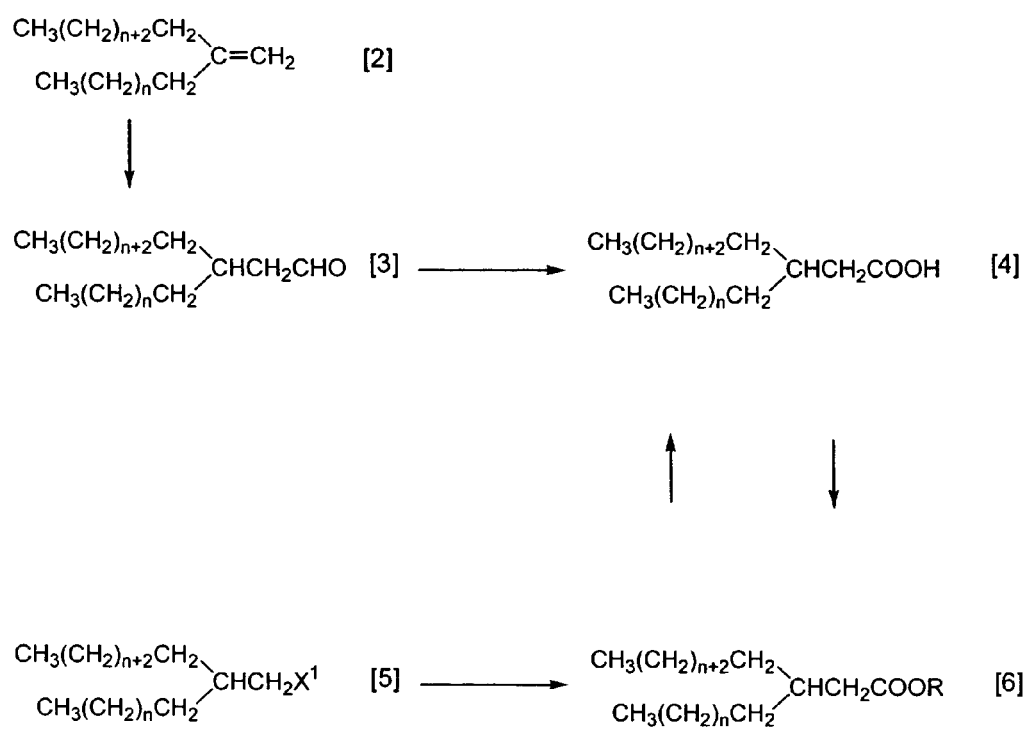
FIG. 1 shows a synthesis scheme for the carbonyl compound of the invention.

The long-chain branched alkyl group-containing primary carbonyl compound of the invention will now be described.
The carbonyl compound of the invention possesses a structure of the following formula [1].

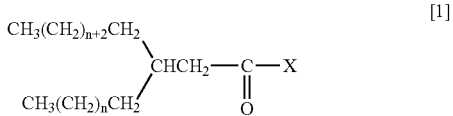

wherein X is hydrogen, a hydroxy group, an alkoxy group, or a group derived from a polyol, and n is 4 to 30.

In formula [1], X is a hydrogen atom, a hydroxy group, an alkoxy group (OR), or a group derived from a polyol. Specifically, when X is a hydrogen atom, the formula represents an aldehyde compound, when X is a hydroxy group, the formula represents a carboxylic compound, and when X is an alkoxy group or a group derived from a polyol, the formula represents an ester compound.

The R in the alkoxy group (OR) represents a hydrocarbon group having 1 to 100 carbon atoms, for example, an alkyl group, alkenyl group, aryl group, or aralkyl group.

As the alkyl group, a linear alkyl group such as a methyl group, ethyl group, n-propyl group, and n-butyl group; a branched alkyl group such as an isobutyl group, isodecyl group, 2-ethylhexyl group, 2-octyl-dodecyl group, neopentyl group, and t-butyl group; and a cyclic alkyl group such as a cyclohexyl group, cyclopentyl group, and cyclopropyl group can be given.

As the alkenyl group, an aryl group, homoaryl group, butenyl group, and the like can be given.

As the aryl group, a phenyl group, tolyl group, naphthyl group, biphenyl group, hydroxybiphenyl group, binaphthyl group, and the like can be given.

As the aralkyl group, a benzyl group, p-tolylmethyl group, p-nitrobenzyl group, p-aminobenzyl group, p-chlorobenzyl group, and the like can be given.

As the other R, a 2-butoxyethyl group, n-propoxyethyl group, or the like having a hetero atom in the main chain can be used.

Of these R, a methyl group, ethyl group, n-propyl group, n-butyl group, isobutyl group, isodecyl group, 2-ethylhexyl group, 2-octyldodecyl group, neopentyl group, t-butyl group, cyclohexyl group, cyclopentyl group, n-hexyl group, n-octyl group, and isostearyl group are preferable, with n-hexyl group, n-octyl group, isostearyl group, isodecyl group, 2-ethylhexyl group, 2-octyldodecyl group, and t-butyl group being particularly preferable.

As the group derived from a polyol, groups derived from polyols such as ethylene glycol, 1,2-butanediol, 1,2-hexanediol, 1,4-cyclohexanediol, 1,5-hexanediol, 1,6-hexanediol, 2,5-hexanediol, diethylene glycol, catechol, biphenol, binaphthol, neopentyl glycol, phytane triol, trimethylolpropane, diglycerol, pentaerythritol, trimethylolethane, and polyglycerol, and groups derived from naturally occurring alcohols such as cholesterol, glucose, fructose, maltose, chitin, chitosan, sorbitol, and mannitol can be given.

Of these, ethylene glycol, 1,2-butanediol, 1,4-hexanediol, 1,5-hexanediol, diethylene glycol, catechol, cholesterol, glucose, neopentyl glycol, trimethylolpropane, and pentaerythritol are preferable, with ethylene glycol, 1,5-hexanediol, diethylene glycol, glucose, neopentyl glycol, trimethylolpropane, trimethylolethane, and pentaerythritol being particularly preferable.

When X is a group derived from a polyol, one or more of the hydroxy groups of the polyol form one or more structures shown by formula [1] by ester bonding.

A carbonyl compound which is an ester compound derived from a hindered alcohol is particularly preferable due to excellent heat resistance and oxidation stability. As specific preferable examples of the hindered alcohol, trimethylolpropane, trimethylolethane, and neopentyl glycol can be given.

In formula [1], n is an integer from 4 to 30. If n is less than 4, the boiling point is low and volatile components are easily released, which causes problems when used as a lubricating oil or lubricating oil additive. If n exceeds 30, viscosity is too high and problems such as solidification occur. n is preferably an integer from 4 to 20, with an even number from 4 to 20 being more preferable, and an even number from 4 to 10 being particularly preferable.

As specific examples of the long-chain branched alkyl group-containing primary aldehyde compound of formula [1], 3-hexylundecanal, 3-octyltridecanal, 3-decylpentadecanal, 3-dodecylheptadecanal, 3-tetradecylnonadecanal, 3-hexadecylicosanal, 3-octadecyltricosanal, 3-eicosylpentacosanal, 3-docosanylheptacosanal, and the like can be given.

As specific examples of the long-chain branched alkyl group-containing primary carboxylic acid of formula [1], 3-hexylundecanoic acid, 3-octyltridecanoic acid, 3-decylpentadecanoic acid, 3-dodecylheptadecanoic acid, 3-tetradecylnonadecanoic acid, 3-hexadecylicosanoic acid, 3-octadecyltricosanoic acid, 3-eicosylpentacosanoic acid, 3-docosanylheptacosanoic acid, and the like can be given.

As specific examples of the long-chain branched alkyl group-containing primary ester compound of formula [1], methyl 3-hexylundecanoate, ethyl 3-hexylundecanoate, n-propyl 3-hexylundecanoate, n-butyl 3-hexylundecanoate, allyl 3-hexylundecanoate, homoallyl 3-hexylundecanoate, 1-butenyl 3-hexylundecanoate, 2-butenyl 3-hexylundecanoate, n-butoxyethyl 3-hexylundecanoate, n-propoxyethyl 3-hexylundecanoate, isobutyl 3-hexylundecanoate, isodecyl 3-hexylundecanoate, 2-ethylhexyl 3-hexylundecanoate, 2-octyldodecyl 3-hexylundecanoate, neopentyl 3-hexylundecanoate, t-butyl 3-hexylundecanoate, cyclohexyl 3-hexylundecanoate, cyclopentyl 3-hexylundecanoate, cyclopropyl 3-hexylundecanoate, phenyl 3-hexylundecanoate, p-tolyl 3-hexylundecanoate, m-tolyl 3-hexylundecanoate, o-tolyl 3-hexylundecanoate, 1-naphthyl 3-hexylundecanoate, 2-naphthyl 3-hexylundecanoate, biphenyl 3-hexylundecanoate, benzyl 3-hexylundecanoate, 1,4-cyclohexanediol 3-hexylundecanoates, catechol 3-hexylundecanoates, biphenol 3-hexylundecanoates, binaphthol 3-hexylundecanoates, ethylene glycol 3-hexylundecanoates, 1,2-butanediol 3-hexylundecanoates, 1,5-hexanediol 3-hexylundecanoates, 1,6-hexanediol 3-hexylundecanoates, 2,5-hexanediol 3-hexylundecanoates, diethylene glycol 3-hexylundecanoates, neopentyl glycol 3-hexylundecanoates, 1,4-phytanetriol 3-hexylundecanoates, trimethylolpropane 3-hexylundecanoates, diglycerol 3-hexylundecanoates, pentaerythritol 3-hexylundecanoates, polyglycerol 3-hexylundecanoates, cholesterol 3-hexylundecanoates, glucose 3-hexylundecanoates, fructose 3-hexylundecanoates, maltose 3-hexylundecanoates, chitin 3-hexylundecanoates, chitosan 3-hexylundecanoates, sorbitol 3-hexylundecanoates, mannitol 3-hexylundecanoates, methyl 3-octyltridecanoate, ethyl 3-octyltridecanoate, n-propyl 3-octyltridecanoate, n-butyl 3-octyltridecanoate, allyl 3-octyltridecanoate, homoallyl 3-octyltridecanoate, 1-butenyl 3-octyltridecanoate, 2-butenyl 3-octyltridecanoate, n-butoxyethyl 3-octyltridecanoate, n-propoxyethyl 3-octyltridecanoate, isobutyl 3-octyltridecanoate, isodecyl 3-octyltridecanoate, 2-ethylhexyl 3-octyltridecanoate, 2-octyldodecyl 3-octyltridecanoate, neopentyl 3-octyltridecanoate, t-butyl 3-octyltridecanoate, cyclohexyl 3-octyltridecanoate, cyclopentyl 3-octyltridecanoate, cyclopropyl 3-octyltridecanoate, phenyl 3-octyltridecanoate, p-tolyl 3-octyltridecanoate, m-tolyl 3-octyltridecanoate, o-tolyl 3-octyltridecanoate, 1-naphthyl 3-octyltridecanoate, 2-naphthyl 3-octyltridecanoate, biphenyl 3-octyltridecanoate, benzyl 3-octyltridecanoate, 1,4-cyclohexanediol 3-octyltridecanoates, catechol 3-octyltridecanoates, biphenol 3-octyltridecanoates, binaphthol 3-octyltridecanoates, ethylene glycol 3-octyltridecanoates, 1,2-butanediol 3-octyltridecanoates, 1,5-hexanediol 3-octyltridecanoates, 1,6-hexanediol 3-octyltridecanoates, 2,5-hexanediol 3-octyltridecanoates, diethylene glycol 3-octyltridecanoates, neopentyl glycol 3-octyltridecanoates, 1,4-phytanetriol 3-octyltridecanoates, trimethylolpropane 3-octyltridecanoates, diglycerol 3-octyltridecanoates, pentaerythritol 3-octyltridecanoates, polyglycerol 3-octyltridecanoates, cholesterol 3-octyltridecanoates, glucose 3-octyltridecanoates, fructose 3-octyltridecanoates, maltose 3-octyltridecanoates, chitin 3-octyltridecanoates, chitosan 3-octyltridecanoates, sorbitol 3-octyltridecanoates, mannitol 3-octyltridecanoates, methyl 3-decylpentadecanoate, ethyl 3-decylpentadecanoate, n-propyl 3-decylpentadecanoate, n-butyl 3-decylpentadecanoate, allyl 3-decylpentadecanoate, homoallyl 3-decylpentadecanoate, 1-butenyl 3-decylpentadecanoate, 2-butenyl 3-decylpentadecanoate, an-butoxyethyl 3-decylpentadecanoate, n-propoxyethyl 3-decylpentadecanoate, isobutyl 3-decylpentadecanoate, isodecyl 3-decylpentadecanoate, 2-ethylhexyl 3-decylpentadecanoate, 2-octyldodecyl 3-decylpentadecanoate, neopentyl 3-decylpentadecanoate, t-butyl 3-decylpentadecanoate, cyclohexyl 3-decylpentadecanoate, cyclopentyl 3-decylpentadecanoate, cyclopropyl 3-decylpentadecanoate, phenyl 3-decylpentadecanoate, p-tolyl 3-decylpentadecanoate, m-tolyl 3-decylpentadecanoate, o-tolyl 3-decylpentadecanoate, 1-naphthyl 3-decylpentadecanoate, 2-naphthyl 3-decylpentadecanoate, biphenyl 3-decylpentadecanoate, benzyl 3-decylpentadecanoate, 1,4-cyclohexanediol 3-decylpentadecanoates, catechol 3-decylpentadecanoates, biphenol 3-decylpentadecanoates, binaphthol 3-decylpentadecanoates, ethylene glycol 3-decylpentadecanoates, 1,2-butanediol 3-decylpentadecanoates, 1,5-hexanediol 3-decylpentadecanoates, 1,6-hexanediol 3-decylpentadecanoates, 2,5-hexanediol 3-decylpentadecanoates, diethylene glycol 3-decylpentadecanoates, neopentyl glycol 3-decylpentadecanoates, 1,4-phytanetriol 3-decylpentadecanoates, trimethylolpropane 3-decylpentadecanoates, diglycerol 3-decylpentadecanoates, pentaerythritol 3-decylpentadecanoates, polyglycerol 3-decylpentadecanoates, cholesterol 3-decylpentadecanoates, glucose 3-decylpentadecanoates, fructose 3-decylpentadecanoates, maltose 3-decylpentadecanoates, chitin 3-decylpentadecanoates, chitosan 3-decylpentadecanoates, sorbitol 3-decylpentadecanoates, mannitol 3-decylpentadecanoates, methyl 3-dodecylheptadecanoate, ethyl 3-dodecylheptadecanoate, n-propyl 3-dodecylheptadecanoate, n-butyl 3-dodecylheptadecanoate, allyl 3-dodecylheptadecanoate, homoallyl 3-dodecylheptadecanoate, 1-butenyl 3-dodecylheptadecanoate, 2-butenyl 3-dodecylheptadecanoate, n-butoxyethyl 3-dodecylheptadecanoate, n-propoxyethyl 3-dodecylheptadecanoate, isobutyl 3-dodecylheptadecanoate, isodecyl 3-dodecylheptadecanoate, 2-ethylhexyl 3-dodecylheptadecanoate, 2-octyldodecyl 3-dodecylheptadecanoate, neopentyl 3-dodecylheptadecanoate, t-butyl 3-dodecylheptadecanoate, cyclohexyl 3-dodecylheptadecanoate, cyclopentyl 3-dodecylheptadecanoate, cyclopropyl 3-dodecylheptadecanoate, phenyl 3-dodecylheptadecanoate, p-tolyl 3-dodecylheptadecanoate, m-tolyl 3-dodecylheptadecanoate, o-tolyl 3-dodecylheptadecanoate, 1-naphthyl 3-dodecylheptadecanoate, 2-naphthyl 3-dodecylheptadecanoate, biphenyl 3-dodecylheptadecanoate, benzyl 3-dodecylheptadecanoate, 1,4-cyclohexanediol 3-dodecylheptadecanoates, catechol 3-dodecylheptadecanoates, biphenol 3-dodecylheptadecanoates, binaphthol 3-dodecylheptadecanoates, ethylene glycol 3-dodecylheptadecanoates, 1,2-butanediol 3-dodecylheptadecanoates, 1,5-hexanediol 3-dodecylheptadecanoates, 1,6-hexanediol 3-dodecylheptadecanoates, 2,5-hexanediol 3-dodecylheptadecanoates, diethylene glycol 3-dodecylheptadecanoates, neopentyl glycol 3-dodecylheptadecanoates, 1,4-phytanetriol 3-dodecylheptadecanoates, trimethylolpropane 3-dodecylheptadecanoates, diglycerol 3-dodecylheptadecanoates, pentaerythritol 3-dodecylheptadecanoates, polyglycerol 3-dodecylheptadecanoates, cholesterol 3-dodecylheptadecanoates, glucose 3-dodecylheptadecanoates, fructose 3-dodecylheptadecanoates, maltose 3-dodecylheptadecanoates, chitin 3-dodecylheptadecanoates, chitosan 3-dodecylheptadecanoates, sorbitol 3-dodecylheptadecanoates, mannitol 3-dodecylheptadecanoates, and the like can be given.

Although examples of the long-chain branched alkyl group-containing primary ester compound wherein n in formula [1] is 4, 6, 8, and 10 were given, n is not limited to these and n can be properly selected from the above range.

The following is a description of the method for producing the carbonyl compound shown by the formula [1] of the invention.

FIG. 1 shows a synthesis scheme for the carbonyl compound of the invention.

An α-olefin compound shown by the formula $CH_3(CH_2)_{n+2}CH=CH_2$ (wherein n is 4 to 30) is used as a starting compound. This compound is used to synthesize a vinylidene compound of the formula [2] of FIG. 1. The vinylidene compound is synthesized by dimerizing the starting compound using a metallocene catalyst and the like (step a).

As examples of the metallocene catalyst, zirconocene dichloride, bis (n-butylcyclopentadienyl) zirconium dichloride, bisindenylzirconium dichloride, bis(2-phenylindenyl) zirconium dichloride, dimethylsilylenebiscyclopentadienylzirconium dichloride, ethylenebisindenylzirconium dichloride, dimethylsilylenebisindenylzirconium dichloride, and isopropylidenebiscyclopentadienylzirconium dichloride can be used.

An aldehyde compound (FIG. 1, formula [3]) and carboxylic compound (FIG. 1, formula [4]) can be obtained by carbonylation of this vinylidene compound.

Specifically, a step of reacting the vinylidene compound of formula [2] with carbon monoxide and hydrogen under oxo reaction conditions to synthesize an aldehyde compound of the following formula [3] (step b), and a step of oxidizing the aldehyde compound of formula [3] under oxidizing reaction conditions to synthesize a carboxylic compound of formula [4] (step c) can be given.

As other methods for synthesizing the carboxylic compound of formula [4], a method comprising Vilsmeyer reaction of a dimerized vinylidene compound of an α-olefin, a method comprising preparing a nucleophilic compound such as a Grignard reagent and lithium reagent from a corresponding halide and reacting the nucleophilic compound with carbon dioxide, dimethyl carbonate, dimethylformamide, and the like to obtain the objective carboxylic acid, and the like can be given.

As a method for obtaining the ester compound (Formula [6] of FIG. 1), a method comprising reacting a nucleophilic reagent such as a Grignard reagent and lithium reagent prepared from a corresponding halide (Formula [5] of FIG. 1) with a carbonic ester such as dimethyl carbonate, a method of heat dehydrating the carboxylic acid (Formula [4] of FIG. 1) obtained by the above method and an alcohol in the presence of an acid or base catalyst, a method of preparing an acid chloride from a carboxylic acid using a thionyl chloride or the like followed by reacting with an alcohol, and the like can be given.

The carbonyl compound of the invention is excellent in low temperature fluidity and biodegradability and possesses a high boiling point. Therefore, the carbonyl compound can be suitably used as an additive for synthetic lubricant.

The synthetic lubricant of the invention contains the carbonyl compound of the above formula [1]. Of these carbonyl compounds, methyl 3-octyltridecanoate, 3-octyltridecanoic acid, isobutyl 3-octyltridecanoate, 2-ethylhexyl 3-octyltridecanoate, 1,5-hexanediol 3-octyltridecanoates, neopentyl glycol 3-octyltridecanoates, trimethylolpropane 3-octyltridecanoates, pentaerythritol 3-octyltridecanoates, methyl 3-hexylundecanoate, 3-hexylundecanoic acid, 3-hexylundecanal, isobutyl 3-hexylundecanoate, 2-ethylhexyl 3-hexylundecanoate, 1,5-hexanediol 3-hexylundecanoate, neopentyl glycol 3-hexylundecanoates, trimethylolpropane 3-hexylundecanoates, methyl 3-decylpentadecanoate, 3-decylpentadecanoic acid, 3-decylpentadecanal, and isobutyl 3-decylpentadecanoate are preferable. Methyl 3-octyltridecanoate, 3-octyltridecanoic acid, 3-octyltridecanal, isobutyl 3-octyltridecanoate, 2-ethylhexyl 3-octyltridecanoate, 1,5-hexanediol 3-octyltridecanoate, neopentyl glycol 3-octyltridecanoates, trimethylolpropane 3-octyltridecanoates, and pentaerythritol 3-octyltridecanoates are particularly preferable.

As other components to be included in the synthetic lubricant, base oils, detergent-dispersants, and viscosity controllers commonly used in lubricating oils can be given.

The synthetic lubricant of the invention possesses excellent lubricating properties and has only a small impact on the environment due to the use of a long-chain branched alkyl group containing primary carbonyl compound excelling in low temperature fluidity and biodegradability and possessing a high boiling point. The lubricating oil can therefore be suitably used in engines, chain saws, bearing oils, cutting oils, and the like.

Of the carbonyl compounds of the invention, carbonyl compounds of the formula [1] wherein X is an alkoxy group (—OR) and R is a hydrocarbon group having 6 to 30 carbon atoms can be suitably used as a cosmetic base material and plasticizer.

As the cosmetic base material, 2-octyldodecyl 3-octyl-tridecanoate, isostearyl 3-octyl-tridecanoate, 2-ethylhexyl 3-octyl-tridecanoate, octyldodecyl 3-octyl-tridecanoate, hexyl 3-octyl-tridecanoate, hexyldecyl 3-octyl-tridecanoate, and cyclohexyl 3-octyl-tridecanoate are preferable.

As the plasticizer, octyl 3-octyl-tridecanoate, 2-ethylhexyl 3-octyl-tridecanoate, isodecyl 3-octyl-tridecanoate, tridecyl 3-octyl-tridecanoate, isononyl 3-octyl-tridecanoate, decyl 3-octyl-tridecanoate, isostearyl 3-octyl-tridecanoate, and stearyl 3-octyl-tridecanoate are preferable.

EXAMPLES

The invention will now be described by way of examples which should not be construed as limitations to the invention.

The compounds were identified and evaluated by the following method.

(1) NMR

Measurement was conducted using JNM-LA500 (manufactured by JEOL Ltd.).

(2) GC-MS

Using helium as a carrier gas and a DB-1HT column, the temperature was increased from 100 to 330° C. at a rate of 10° C. per minute. Detection methods EI and CI were used.

(3) Evaluation of Biodegradability

Measurement was conducted in accordance with JIS K6950 using a BOD tester (manufactured by Taitec Co., Ltd.) under conditions of a sample concentration of 100 ppm, activated sludge concentration of 30 ppm, and a temperature of 25° C. over a period of 28 days. Return sludge from the Matsugashima sewage treatment plant in Ichihara City was used as the activated sludge.

Example 1

As the ester compound of the invention, methyl 3-octyl-tridecanoate was synthesized.

[Synthesis Method]

10 g (33.49 mmol) of 2-octyldodecanol (manufactured by Aldrich) and 8.8 g (33.5 mmol) of triphenylphosphine (manufactured by Kanto Chemical Co., Ltd.) were dissolved in 100 ml of dehydrated dichloromethane and cooled with ice. After gradually adding 6.0 g (33.9 mmol) of N-bromosuccinimido (manufactured by Wako Pure Chemicals Co., Ltd.), the mixture was stirred for three hours at room temperature. The solvent was evaporated under reduced pressure, hexane was added to the residue, and the precipitate was filtrated. The filtrate was concentrated to obtain 10.0 g (27.6 mmol) of 2-octyl-1-bromododecane.

3 g (123.3 mmol) of magnesium was suspended in 30 ml of a dehydrated tetrahydrofuran solution under nitrogen atmosphere to activate the magnesium with dibromoethane. 120 ml of a dehydrated tetrahydrofuran solution comprising 8.0 g (22.1 mmol) of the synthesized 2-octyl-1-bromododecane was added to this solution by dropping. After dropping, the solution was stirred for two hours. The reaction mixture was cooled with ice, 2.0 ml (23.7 mmol) of dimethyl carbonate was added, and the mixture was stirred overnight at room temperature (25° C.). After filtering the reaction solution, adding diluted hydrochloric acid to the filtrate, and extracting using hexane, the solvent was evaporated under reduced pressure. The residue was distilled under the conditions of 0.15 mmHg and an oil bath temperature of 180 to 190° C. to obtain 5.0 g (14.7 mmol) of methyl 3-octyl-tridecanoate as a colorless oil. The fluidity of this compound did not decrease even when cooled to −20° C.

The results of $^1$H-NMR, $^{13}$C-NMR, and GC-MS analysis of the synthesized methyl 3-octyl-tridecanoate are shown below.

[$^1$H-NMR(CDCl$_3$)]
0.88(t, J=14 Hz, 6H, CH$_3$), 1.26(CH$_2$, 32H), 1.84(m, 1H, CH), 2.23(d, J=14 Hz, 2H, CH$_2$CO), 3.65(s, 3H, OCH$_3$)

[$^{13}$C-NMR (CDCl$_3$)]
14.00(CH$_3$): 22.58(CH$_2$-CH$_3$): 26.41, 29.20, 29.24, 29.47, 29.51, 29.78, 31.81, 33.79 (CH$_2$): 34.95(CH): 38.99(CH$_2$C=O): 51.21(OCH$_3$): 174.03(C=O)

[GC-MS]341(M$^+$+1), 227(M$^+$−(C$_8$H$_{17}$)+1), 199(M$^+$−(C$_{10}$H$_{21}$)+1)

Example 2

As the carboxylic compound of the invention, 3-octyl-tridecanoic acid was synthesized.

[Synthesis Method]30 ml of an aqueous solution containing 1.7 g (43.5 mmol) of potassium hydroxide was added to 5.0 g (14.7 mmol) of methyl 3-octyl-tridecanoate under nitrogen atmosphere and heated at 80° C. for five hours. After acidifying the reaction solution with diluted hydrochloric acid, extraction was conducted using ether to obtain 4.2 g (13.1 mmol) of 3-octyl-tridecanoic acid as a colorless oil.

The fluidity of this compound did not decrease even when cooled to −20° C. and the compound excelled in low temperature fluidity.

The pour point of 3-octyl-tridecanoic acid was measured in accordance with JIS K2269. The pour point was determined to be −37° C. On the other hand, the pour point of a similar compound isostearic acid (2-n-heptylundecanoic acid) was −20° C. ("14303 Chemical Products", The Chemical Daily Co., Ltd.). Another similar compound 2-octyldodecanoic acid was a solid having a melting point of 35° C.

The above results confirm that the 3-octyl-tridecanoic acid of the invention excels in low temperature fluidity even though it has a large molecular weight.

The results of $^1$H-NMR, $^{13}$C-NMR, and GC-MS analysis of the synthesized 3-octyl-tridecanoic acid are shown below.

[$^1$H-NMR(CDCl$_3$)]
0.88(t, J=14.0 Hz, 6H, CH$_3$), 1.26(32H, CH$_2$), 1.84(m, 1H, CH), 2.26(d, J=13.0 Hz, 2H, CH$_2$CO)

[$^{13}$C-NMR (CDCl$_3$)]
14.00(CH$_3$): 22.59(CH$_2$-CH$_3$): 26.39, 29.21, 29.26, 29.48, 29.54, 29.78, 31.80, 33.67(CH$_2$): 34.77(CH): 38.94(CH$_2$CO): 179.53(C=O)

[GC-MS]
326(M$^+$), 213(M$^+$−(C$_8$H$_{17}$)), 141(M$^+$−(C$_{10}$H$_{21}$))

Example 3

As the aldehyde compound of the invention, 3-octyl-tridecanal was synthesized.

[Synthesis Method]
3 g (123.3 mmol) of magnesium was suspended in 30 ml of a dehydrated tetrahydrofuran solution under nitrogen atmosphere to activate the magnesium with dibromoethane.

120 ml of a dehydrated tetrahydrofuran solution comprising 8.0 g (22.1 mmol) of 2-octyl-1-bromododecane obtained by the method of Example 1 was added to this solution by dropping and after the completion of dropping, the mixture was stirred for two hours. After the reaction mixture was cooled with ice and 5.0 ml (66.3 mmol) of dehydrated dimethylformamide (manufactured by Kanto Chemical Co., Ltd.) was added, the mixture was stirred overnight at room temperature (25° C.). Diluted hydrochloric acid was added to the filtrate, extraction was conducted using hexane, and the solvent was evaporated under reduced pressure. The residue was distilled under vacuum to obtain 3-octyl-tridecanal as a colorless oil.

This compound has the fluidity even when cooled to −20° C.

The results of $^1$H-NMR, $^{13}$C-NMR, and GC-MS analysis of the synthesized 3-octyl-tridecanal are shown below.

[$^1$H-NMR(CDCl$_3$)]
0.88(t, J=14 Hz, 6H, CH$_3$), 1.26(CH$_2$, 32H), 1.95(m, 1H, CH), 2.32(dd, J=6.7, 2.4 Hz, 2H, CH$_2$C(O)H), 9.75(t, J=2.4 Hz, 1H, C(O)H)

[$^{13}$C-NMR(CDCl$_3$)]
14.00(CH$_3$): 22.55(CH$_2$-CH$_3$): 26.56, 29.18, 29.23, 29.44, 29.49, 29.74, 31.77, 34.08(CH$_2$): 32.91(CH): 48.51(CH$_2$—C(O)H), 203.17(C=O)

[GC-MS]
311(M$^+$+1)

The biodegradability of the methyl 3-octyl-tridecanoate synthesized in Example 1, the 3-octyl-tridecanoic acid synthesized in Example 2, and methyl 2-ethylhexanoate (synthesized from 2-ethylhexanoic acid (manufactured by Wako Pure Chemicals Co., Ltd.) and methanol using a common method) as Comparative Example 1 were evaluated. The results are shown in Table 1.

TABLE 1

| Compound | Biodegradation (%) |
| --- | --- |
| 3-Octyl-tridecanoic acid (Example 2) | 62.7 |
| Methyl 3-octyl-tridecanoate (Example 1) | 52.3 |
| Methyl 2-ethylhexanoate (Comparative Example 1) | 25.7 |

The results of Table 1 confirm that the long-chain branched alkyl group-containing primary carbonyl compound of the invention exhibited high biodegradability.

Example 4

As an ester using a hindered alcohol, trimethylolpropane tri(3-octyl-tridecanoate) was synthesized.

[Synthesis Method]

80 ml of toluene as a solvent and 76.4 ml (1.04 mol) of thionyl chloride were added to a 500 ml four neck flask equipped with a stirrer, thermometer, dropping funnel, and Dimroth condenser with a gas emission tube. The mixture was maintained at 55° C. under nitrogen atmosphere.

A mixed solution of 285 g (0.873 mol) of the 3-octyl-tridecanoic acid synthesized in Example 2 and 20 ml of toluene was gradually dropped while stirring. As a result, $SO_2$ gas and HCl gas were generated with heat release. The gas production stopped after about one hour. The Dimroth condenser was replaced with a distillation head and the temperature was increased to 95° C. to remove excess thionyl chloride. An acid halide of 3-octyl-tridecanoic acid was thereby obtained.

The distillation head was replaced with the Dimroth condenser and a mixed solution of 39 g (0.29 mol) of trimethylolpropane (1,1,1-tris(hydroxymethyl)propane, manufactured by Wako Pure Chemicals Co., Ltd.) and 75 ml of dehydrated pyridine was slowly dropped. After refluxing for four hours, the solution was cooled to room temperature. The precipitated pyridine hydrochloride was filtered from the reaction solution and the filtrate was poured into 500 ml of water. Using a separating funnel, the filtrate was washed twice with water and three times with an aqueous solution of sodium bicarbonate, and the organic layer was dried using anhydrous magnesium sulfate. The desiccant was removed by filtration and the solvent was evaporated to obtain 302 g of a light yellow clear liquid.

The results of $^1$H-NMR analysis of the synthesized trimethylolpropane tri (3-octyl-tridecanoate) are shown below.

[$^1$H-NMR(CDCl$_3$)]

0.90(21H, CH$_3$), 1.29(50H, CH$_2$), 2.35(6H, CH$_2$CO), 4.00 (s, 6H, CH$_2$O)

The oxidation stability of the above synthesized triester was tested and the viscosity before and after testing was measured. The oxidation stability test was conducted in accordance with JIS K2514, wherein the kinematic viscosity was measured at 40° C. and 100° C. after heating for 24 hours at 140° C. in the presence of copper and steel catalysts. The compounds showing a small change (increase) in kinematic viscosity were regarded as excelling in oxidation stability.

The pour point which indicates the characteristics of the ester of the invention was measured in accordance with JIS K2269. The results are shown in Table 2.

A commercially available trimethylolpropane trioleate as Comparative Example 2 was tested in the same manner.

TABLE 2

|  | Trimethylolpropane tri(3-octyl-tridecanoate) (Example 4) | | Trimethylolpropane trioleate (Comparative Example 2) | |
| --- | --- | --- | --- | --- |
|  | Kinematic viscosity at 40° C. (mm$^2$/s) | Kinematic viscosity at 100° C. (mm$^2$/s) | Kinematic viscosity at 40° C. (mm$^2$/s) | Kinematic viscosity at 100° C. (mm$^2$/s) |
| Before heating | 62.76 | 9.95 | 47.96 | 9.66 |
| After heating at 140° C. for 24 hours | 67.28 | 10.24 | 60.91 | 11.24 |
| Change in kinematic viscosity | 1.07 | 1.03 | 1.27 | 1.16 |
| Pour point (° C.) | −50 or less | | −47.5 | |

As shown in Table 2, the carbonyl compound of the invention trimethylolpropane tri(3-octyltridecanoate) (Example 4) exhibited a smaller change in kinematic viscosity after heating and more excellent oxidation stability than the trimethylolpropane trioleate (Comparative Example). Also, the ester of Example 4 exhibited more excellent low temperature fluidity than the ester of the Comparative Example and can be suitably used as a base oil for a lubricating oil.

Example 5

As a cosmetic base, 2-octyldodecyl 3-octyl-tridecanoate was prepared and evaluated.

[Synthesis Method]

In the same manner as in Example 4, an acid halide was prepared using 285 g (0.873 mol) of 3-octyl-tridecanoic acid.

A mixed solution of 250 g (0.873 mol) of 2-octyl-1-dodecanol and 75 ml of dehydrated pyridine was slowly dropped. After refluxing for four hours, the solution was cooled to room temperature. The precipitated pyridine hydrochloride was filtered from the reaction solution and the filtrate was poured into 500 ml of water. Using a separating funnel, the filtrate was washed twice with water and three times with an aqueous solution of sodium bicarbonate, and the organic layer was dried using anhydrous magnesium sulfate. The desiccant was removed by filtration and column treatment was conducted to obtain 480 g of the objective product as a colorless oil.

The results of $^1$H-NMR analysis of the synthesized 2-octyldodecyl 3-octyl-tridecanoate are shown below.

[$^1$H-NMR(CDCl$_3$)]

0.92(12H, CH$_3$), 1.30(70H, CH$_2$), 2.30(2H, CH$_2$CO), 3.98 (2H, CH$_2$O)

The 2-octyldodecyl 3-octyl-tridecanoate synthesized above and 2-octyldodecyl isostearate wherein the carboxylic acid portion is isostearic acid as Comparative Example 3 were synthesized in the same manner as in Example 5 and the biodegradability thereof was evaluated.

The results are shown in Table 3.

TABLE 3

| Compound | Biodegradation (%) |
| --- | --- |
| 2-Octyldodecyl 3-octyl-tridecanoate (Example 5) | 50.1 |
| 2-Octyldodecyl isostearate (Comparative Example 3) | 39.5 |

Table 3 confirmed that the 2-octyldodecyl 3-octyl-tridecanoate obtained in Example 5 exhibited excellent biodegradability, was mild to the skin, exhibited good spreadability, and could be suitably used as a base for various cosmetics.

Example 6

The method for manufacturing a carbonyl compound of the invention (synthesis of oxocarboxylic acid from α-olefin) was conducted.

(1) Dimerization of 1-decene Using Metallocene Complex 1-decene (3.0 kg), zirconocene dichloride (metallocene complex: 0.9 gram, 3 mmol), and methyl alumoxane (manufactured by Albemarle Corporation, 8 mmol (Al-reduced)) were added one after the other to a 5 l three neck flask in which the inner air had been replaced with nitrogen and the mixture was stirred at room temperature (up to 20° C.). The color of the reaction solution changed from yellow to reddish brown. After reacting for 48 hours, methanol was added to terminate the reaction. Next, hydrochloric acid aqueous solution was added to the reaction solution, and the organic layer was washed.

The organic layer was distilled under reduced pressure to obtain 2.5 kg of a dimerized fraction. Gas chromatography and GC-MS analysis of this fraction confirmed a dimerized vinylidene olefin purity of 97% and an absence of alkanes.

(2) Synthesis of 3-octyl-tridecanal Using an Oxo Reaction 20 ml of toluene, hydrocarbonyltris(triphenylphosphine)rhodium (I) (91.8 mg, 0.01 mmol, manufactured by Strem Chemicals, Inc.), and 18 g (64 mmol) of the vinylidene compound synthesized in (1) above were added to an autoclave in which the inner air had been replaced with nitrogen. The mixture was reacted with a mixed gas of hydrogen/carbon monoxide (1:1 molar ratio) under a mixed gas pressure of 2.5 MPa at 80° C. for 15 hours. After cooling the autoclave and releasing the pressure, sodium hydroxide aqueous solution was added and stirred. After removing the reaction mixture and separating the organic layer, the organic layer was dried with anhydrous magnesium sulfate and distilled under reduced pressure to obtain 14.1 g of the objective product. Gas chromatography analysis confirmed a purity of 96% and $^1$H-NMR and $^{13}$C-NMR analysis confirmed the same results as obtained for the compound of Example 3.

(3) Synthesis of 3-octyl-tridecanoic Acid by Oxidizing 3-octyl-tridecanal 14 g of 3-octyl-tridecanal and 1 ml of a 53% cobalt naphthenate mineral oil solution (Co content: 6%; manufactured by Strem Chemicals Inc) were added to a glass reactor and reacted at a temperature of 60° C. for eight hours while blowing air at a rate of 6 l/h. The reaction was terminated and the reaction solution was washed with water and distilled under reduced pressure to obtain 12.3 g of 3-octyl-tridecanoic acid as the objective product.

Gas chromatography analysis confirmed a purity of 94% and $^1$H-NMR and $^{13}$C-NMR analysis confirmed the same results as obtained for the compound of Example 2.

Reference Example 1-decene was dimerized using triethylaluminum.

1-decene (300 g) and triethylaluminum (3.6 g, 32 mmol) were added under nitrogen atmosphere to a 1.0 l autoclave in which the inner air had been replaced with nitrogen and heated at 185° C. for 12 hours. After the reaction, the reaction mixture was cooled to normal temperature and methanol was gradually added while stirring under nitrogen atmosphere.

The contents were removed and washed with a hydrochloric acid aqueous solution to obtain an organic layer. The organic layer was distilled under reduced pressure to obtain 240 g of a dimerized fraction.

Gas chromatography and GC-MS analysis of this fraction confirmed a dimerized vinylidene olefin proportion of 80%, an isomerized olefin proportion of 6%, and alkane proportion of 10%. The compound possessed a lower purity than the compound obtained by the manufacturing method of the invention in Example 6.

Example 7

As a resin modifier (plasticizer), octyl 3-octyl-tridecanoate was prepared and evaluated.

[Synthesis Method]

In the same manner as in Example 4, an acid halide was prepared using 285 g (0.873 mol) of 3-octyl-tridecanoic acid.

A mixed solution of 113.7 g (0.873 mol) of octanol and 75 ml of dehydrated pyridine was slowly dropped. After refluxing for four hours, the solution was cooled to room temperature. The precipitated pyridine hydrochloride was filtered from the reaction solution and the filtrate was poured into 500 ml of water. Using a separating funnel, the filtrate was washed twice with water and three times with an aqueous solution of sodium bicarbonate, and the organic layer was dried using anhydrous magnesium sulfate. The desiccant was removed by filtration and the filtrate was subjected to column treatment to obtain 317 g of the objective product as a colorless oil.

The results of $^1$H-NMR analysis of the synthesized octyl 3-octyl-tridecanoate are shown below.

[$^1$H-NMR(CDCl$_3$)]

0.91(9H, CH$_3$), 1.30(44H, CH$_2$), 2.29(2H, CH$_2$CO), 3.98 (2H, CH$_2$O)

The octyl 3-octyl-tridecanoate synthesized above and octyl oleate synthesized using a conventional method as Comparative Example 4 were evaluated for a resin modifier (plasticizer).

As the plasticizer evaluation, loss on heat was evaluated. In accordance with JIS K6751-4, the decrease in amount after heating at 125° C. for three hours was used as the heating loss.

The evaluation results are shown in Table 4.

TABLE 4

| Compound | Decrease in amount after heating (%) |
| --- | --- |
| Octyl 3-octyl-tridecanoate (Example 7) | 0.10 |
| Octyl oleate (Comparative Example 4) | 0.30 |

The oxidation stability was evaluated in the same manner as in Example 4. The evaluation results are shown in Table 5.

TABLE 5

|  | Octyl 3-octyl-tridecanoate (Example 7) Kinematic viscosity at 40° C. (mm²/s) | Octyl oleate (Comparative Example 4) Kinematic viscosity at 40° C. (mm²/s) |
|---|---|---|
| Before heating | 20.08 | 15.33 |
| After heating at 140° C. for 24 hours | 21.74 | 19.89 |
| Change in kinematic viscosity | 1.04 | 1.29 |

The above evaluation results show that the carbonyl compound of the invention exhibited a small loss on heat, excelled in oxidation stability, and could be suitably used as a reformer (plasticizer) for epoxy resins and the like.

Since epoxy resins normally have a high viscosity thereby making them hard to work with, plasticizers and diluents are added to lower the viscosity for use.

INDUSTRIAL APPLICABILITY

The long-chain branched alkyl group-containing primary carbonyl compound of the invention excels in low temperature fluidity and biodegradability and possesses a high boiling point. The compound can therefore be suitably used in lubricating oils, lubricating oil additives, paints, resin reformers, plasticizers, cosmetic base materials, and the like.

The invention claimed is:

1. A carbonyl compound represented by the following formula [1],

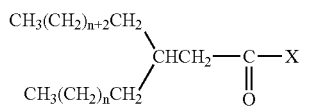

wherein X is hydrogen, a hydroxy group, an alkoxy group or a group derived from a polyol, and n, which is the same in each instance, is 4 to 30 and wherein, n does not equal 8.

2. The carbonyl compound according to claim 1 wherein n of the formula [1] is 4 to 20.

3. The carbonyl compound according to claim 1 wherein n of the formula [1] is an even number of 4 to 10.

4. The carbonyl compound according to claim 1 wherein n of the formula [1] is 6.

5. The carbonyl compound according to claim 1 wherein X of the formula [1] is an alkoxy group (—OR) and R is a hydrocarbon group with 6 to 30 carbon atoms.

6. The carbonyl compound according to claim 1 which is an ester compound derived from a hindered alcohol.

7. The carbonyl compound according to claim 6 wherein the hindered alcohol is a compound selected from trimethylolpropane, trimethylolethane, and neopentylglycol.

8. A synthetic lubricant comprising the carbonyl compound according to any one of claims 1 to 7.

9. A cosmetic base material comprising the carbonyl compound of claim 5.

10. A plasticizer comprising the carbonyl compound of claim 5.

11. A method for producing a acarbonyl compound represented by the following formula [1],

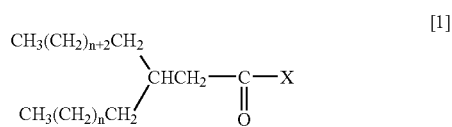

wherein X is hydrogen, a hydroxy group, an alkoxy group or a group derived from a polyol, and n, which is the same in each instance, is 4 to 30, comprising:

(a) dimerizing a compound represented by $CH_3(CH_2)_{n+2}CH_2CH=CH_2$ (wherein n is 4 to 30) by using a metallocene catalyst to synthesize a vinylidene compound of the following formula [2], and (b) reacting the vinylidene compound of the following formula [2] with carbon monoxide and hydrogen under oxo reaction conditions to synthesize an aldehyde compound of the following formula [3]

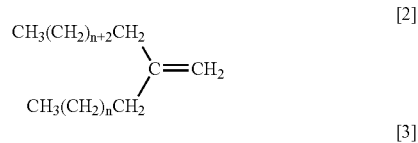

12. The method according to claim 11 further comprising:

(c) oxidizing the aldehyde compound of the formula [3] under oxidizing reaction conditions to synthesize a carboxylic compound of the following formula [4]

13. The carbonyl compound according to claim 1 wherein X is hydrogen.

14. The carbonyl compound according to claim 1 wherein X is a hydroxy group.

15. The carbonyl compound according to claim 1 wherein X an alkoxy group.

16. The carbonyl compound according to claim 1 wherein X is a group derived from a polyol.

* * * * *